US010010077B2

(12) United States Patent
Pszczolkowski et al.

(10) Patent No.: US 10,010,077 B2
(45) Date of Patent: Jul. 3, 2018

(54) GINKGO DERIVED COMPOSITIONS AND THEIR USE TO PREVENT FRUIT INFESTATION BY CODLING MOTH

(71) Applicant: Missouri State University, Springfield, MO (US)

(72) Inventors: Maciej A. Pszczolkowski, Mountain Cove, MO (US); Kevin Durden, Fayetteville, AR (US); Samantha Sellars, Springfield, MO (US); Brian Cowell, Fayetteville, AR (US); John J. Brown, Pullman, WA (US)

(73) Assignee: Missouri State University, Springfield, MO (US)

( * ) Notice: Subject to any disclaimer, the term of this patent is extended or adjusted under 35 U.S.C. 154(b) by 127 days.

(21) Appl. No.: 14/024,225

(22) Filed: Sep. 11, 2013

(65) Prior Publication Data
US 2014/0073592 A1 Mar. 13, 2014

Related U.S. Application Data

(60) Provisional application No. 61/699,652, filed on Sep. 11, 2012.

(51) Int. Cl.
*A01N 37/40* (2006.01)
*A01N 43/12* (2006.01)
*A01N 43/16* (2006.01)
*A01N 43/90* (2006.01)
*A01N 65/06* (2009.01)

(52) U.S. Cl.
CPC ............ *A01N 43/16* (2013.01); *A01N 37/40* (2013.01); *A01N 43/12* (2013.01); *A01N 43/90* (2013.01); *A01N 65/06* (2013.01)

(58) Field of Classification Search
None
See application file for complete search history.

(56) References Cited

FOREIGN PATENT DOCUMENTS

WO WO2004/002224 A1 * 1/2004

OTHER PUBLICATIONS

Stasiuk, M., Bartosiewicz, D., Kozubek, A. (2008) Inhibitory effect of some natural and semisynthetic phenolic lipids upon acetylcholinesterase activity. Food Chemistry, vol. 108, p. 996-1001.*
Lee, KR 2002-0070598, Sep. 10, 2002, machine translation.*
Ahlemeyer B, et al., "Neuroprotective effects of Ginkgo biloba extract," Cell Mol Life Sci, 60:1779-92, 2003.
Ahn Y-J, et al. "Potent insecticidal activity of Ginkgo biloba derived trilactone terpenes against Nilaparvata lugens," in: Phytochemicals for Pest Control, ACS Symposium Series, American Chemical Society, 90-105, 1997.
Chao JC, et al. "Effects of Ginkgo biloba extract on cell proliferation and cytotoxicity in human hepatocellular carcinoma cells," World J Gastroentero; 10:37-41, 2004.
Fu-shun Y, et al., "Deterrents extracted from the leaves of Ginkgo biloba: effects on feeding and contact chemoreceptors," Entomol Exp Appl; 54:57-64, 1990.
Gong YF, et al., "Molecular cloning and expression profile analysis of Ginkgo biloba DXS gene encoding 1-deoxy-D-xylulose 5-phosphate synthase, the first committed enzyme of the 2-C-methyl-D-erythritol 4-phosphate pathway," Planta Med; 72:329-35, 2006.
Kim SM, et al., "Identification of class 2 1-deoxy-D-xylulose 5-phosphate synthase and 1-deoxy-D-xylulose 5phosphate reductoisomerase genes from Ginkgo biloba and their transcription in embryo culture with respect to ginkgolide biosynthesis," Planta Med.; 72:234-40, 2006.
Liao Z, et al., "A new geranylgeranyl diphosphate synthase gene from Ginkgo biloba, which intermediates the biosynthesis of the key precursor for ginkgolides," DNA Seq; 15:153-8 2004.
Mahadevan S, et al., "Multifaceted therapeutic benefits of *Ginkgo biloba* L.: chemistry, efficacy, safety, and uses, " J Food Sci; 73:R14-9, 2008.
Major RT, "The ginkgo, the most ancient living tree. The resistance of *Ginkgo biloba* L. to pests accounts in part for the longevity of this species," Science; 157:1270-3, 1967.
Matsumoto T, et al., "Antifeedant activities of *Ginkgo biloba* L. components against the larva of Pieris rapae crucivora," Agric Biol Chem; 51:249-50, 1987.
Onyilagha JC, et al., "Effect of flavonoids on feeding preference and development of the crucifer pest Mamestra configurata Walker," J Chem Ecol; 30:109-24, 2004.
Poullot D, et al., "Is attract and kill technology potent against resistant Lepidoptera?" Pest Manag Sci; 57: 729-36, 2001.
Schultz DJ, et al., "Bioactivity of anacardic acid against Colorado potato beetle (*Leptinotarsa decemlineata*) larvae," J Agric Food Chem; 54:7522-9, 2006.
Shen G, et al., Cloning and characterization of a root-specific expressing gene encoding 3-hydroxy-3-methylglutaryl coenzyme A reductase from Ginkgo biloba, Mol Biol Rep; 33:117-27, 2006.
Shimada T, et al., "Activation of chemically diverse procarcinogens by human cytochrome P-450 1B1," Cancer Res; 56:2979-84, 1996.
Siegers CP, "Cytotoxicity of alkylphenols from Ginkgo biloba," Phytomedicine; 6:281-3, 1999.
Sierpina VS, et al, "Ginkgo biloba," Am Earn Physician; 68:923-6, 2003.
Simmonds MS, "Importance of flavonoids in insect—plant interactions: feeding and oviposition," Phytochemistry; 56:245-52, 2001.
Simmonds MS, "Flavonoid-insect interactions: recent advances in our knowledge," Phytochemistry; 64:21-30, 2003.
van Beek TA, "Chemical analysis of Ginkgo biloba leaves and extracts," J Chromatogr A.; 967:21-55, 2002.
Velasco R, Zharkikh,et al., "The genome of the domesticated apple (Malus × domestica Borkh.)," Nat Genet; 42: 833-9, 2010.
Vogensen Sb, et al., "Preparation of 7-substituted ginkgolide derivatives: potent platelet activating factor (PAF) receptor antagonists," J Med Chem; 46:601-8, 2003.
Wang P, et al., "Cloning and functional analysis of a cDNA encoding Ginkgo biloba farnesyl diphosphate synthase," Mol Cells; 18:150-6, 2004.

(Continued)

*Primary Examiner* — Layla D Berry
(74) *Attorney, Agent, or Firm* — Lathrop & Gage L.L.P.

(57) ABSTRACT

Codling moth, *Cydia pomonella*, (L.), is a cosmopolitan pest of the apple, potentially causing damage to circa 80% of the fruit. Disclosed here are use of extract of *Ginkgo biloba*, or its synthetic metabolites for preventing or treating apple feeding and infestation by neonate larvae of codling moth.

14 Claims, 2 Drawing Sheets

(56) References Cited

OTHER PUBLICATIONS

Wan X, et al., "Production of gamma-linolenic acid in Pichia pastoris by expression of a delta-6 desaturase gene from Cunninghamella echinulata," J Microbiol Biotechnol; 19:1098-102, 2009.

Woerdenbag, HJ, et al., "Adverse effects of herbal drugs," vol. 3. Berlin: Springer; p. 51-66, 1997.

Woerdenbag HJ, et al., "Adverse Effects and Toxicity of Ginkgo biloba," Medicinal and Aromatic Plants—Industrial Profiles, vol. 12, CRC Press; p. 443-452, 2000.

Pszczolkowski, MA, et al. "Effects of Ginko biloba constitutents on Fruit-Infesting Behavior of Codling Moth (cydia pomonella) in Apples," J of Agri and Food Chem, 59, 10879-10886, 2011.

Pszczolkowski, MA, et al., "Coding Moth Feeding Deterrents from Ginkgo Biloba," Etomology ESA 58th Annual Meeting 2010.

Durden, K, et al., "Extracts of Ginkgo biloba or Artemisia species reducing feeding by neonates of codling moth, cydia pomonella (Lepidoptera: Tortricidae), on apple in a laboratory bioassay," J. Entomol. Soc. Brit. Columbia 105, pp. 83-88, Dec. 2008.

\* cited by examiner

Ginkgolic acid 15:0 (CAS 16611-84-0)

Ginkgolide B (CAS 15291-77-7)

Bilobalide (CAS 33570-04-6)

GINKGO DERIVED COMPOSITIONS AND THEIR USE TO PREVENT FRUIT INFESTATION BY CODLING MOTH

RELATED APPLICATIONS

This application claims priority to U.S. Provisional Patent Application No. 61/699,652, filed Sep. 11, 2012, which is incorporated by reference into the present application in its entirety and for all purposes.

BACKGROUND

1. Field of the Invention

The present disclosure pertains to prevention and treatment of insect infestation in plants. More specifically, this disclosure relates to the use of extracts or chemicals from *Ginkgo* or their synthetic counterparts to prevent or to treat insect infestation or invasion.

2. Description of Related Art

The codling moth, *Cydia pomonella*, is a major insect pest for apple trees. If not controlled, it may cause an annual loss of more than 40 billion U.S. dollars globally. The grower has very limited options to control of this insect because during the invasive stage, the neonate larva burrows into the fruit shortly after hatching from eggs where it stays until its development is completed. Additionally, in areas where codling moth have partial third generation, the neonates typically attempt to infest apples during harvest when the use of insecticides is banned. Broad-spectrum organophosphate neurotoxin and azinphos-methyl remain the major control measure against codling moth. However, these insecticides need to be applied in excessive amounts of (e.g., 1.7 kilograms per hectare) because some codling moths have become resistant to azinphos-methyl over the years. Moreover, this pesticide has been linked to health problems of agricultural workers which raise serious concerns from U.S. Environmental Protection Agency (EPA). In fact, this insecticide has been banned in European Union and is to be phased out in some other countries.

Other insecticides have been developed based on natural pathogens of codling moth, such as bacteria or viruses. However, such insecticides are expensive and are not very effective because damages are usually done before the larvae are killed by the insecticides. Other chemical agents also have disadvantages. For instance, pheromones based on behavioral manipulation such as mating disruption or attract-and-kill have been reported. However, such measures do not resolve problems caused by migration of moths from adjacent areas (Wolfgang, 1989) or insecticide resistance (Poullot et al., 2001).

*Ginkgo* trees have long been known to possess exceptional resistance to pests and pathogens (Major, 1967). However, the underlying mechanisms of *Ginkgo*'s natural resistance have not been studied extensively. Two studies have been reported showing deterrent effects of extracts from *Ginkgo* foliage on feeding by two cabbage insect pests, *Pieris brassicae* and *Pieris rapae*, respectively (Matsumoto and Sei, 1987; Fu-shun et al., 1990). Indirect methods used in these studies leave an open question as to whether feeding was actually inhibited, or *Ginkgo* extracts merely acted as a constipation factor. Effects of anacardic acids on insect development and feeding were studied in only one insect species, the Colorado potato beetle (Schultz et al., 2006). Despite the wealth of data about diversity of flavonoids in plants, few of these compounds have been tested against insects and even less is known about their effects on insect feeding (Simmonds, 2001, 2003). There is evidence that some flavonoids have deterrent and anti-feeding effect on the crucifer pest *Mamestra configurata* (Onyilagha et al., 2004). In a single paper, researchers were focused on insecticidal properties of these compounds in a hemipteran (*Nilaparvata lugens*) (Ahn et al., 1997). However, the reactions of codling moth larvae to flavonoids have not been studied. The effects of *Ginkgo* trilactone terpenes on insect feeding have not been studied.

SUMMARY

Compositions and methods are disclosed for preventing infestation of apple trees and fruits by codling moth. Chemicals from *Ginkgo* are shown to affect feeding behavior in codling moth neonates. In one embodiment, it is shown that codling moth neonates avoid apples treated with 10 mg/ml of crude alcohol extracts from *Ginkgo* leaves (Durden et al., 2008).

*Ginkgo biloba*, and its synthetic metabolites are shown here to prevent apple feeding and infestation by neonate larvae of the codling moth, *Cydia pomonella*. The same composition may also be used to treat apple trees that have already been infested by the codling moth. Tests with crude extracts indicate that deterrent constituents of *Ginkgo* are present among alkylphenols, terpene trilactones and flavonol glycosides. Further tests with *Ginkgo* synthetic metabolites of medical importance, such as ginkgolic acids, kaempferol, quercetin, isorhamnetin, ginkgolides and bilobalide, indicate that at least three of these chemicals have feeding deterrent properties. For example, Ginkgolic acid 15:0 prevents fruit infestation at concentrations as low as 1 mg/ml, bilobalide had deterrent effects at 0.1 mg/ml and higher concentrations and ginkgolide B at 10 mg/ml. On the other hand, kaempferol and quercetin appear to promote fruit infestation by codling moth neonates. In one embodiment of the present disclosure, these components that promote fruit infestation by codling moth may be removed from the gingko derived composition, or may be left out of the composition(s) if the composition is made up of synthetic components. This disclosure is the first report showing that *Ginkgo* constituents influence fruit infestation behavior and have potential applications in fruit protection.

Despite a wealth of information about methodology of analysis and extraction of chemicals from *Ginkgo*, the chemistry of *Ginkgo* has received little attention by insect behaviorists, toxicologists and pharmacologists. Most works studying the effects of *Ginkgo* on behavior pertain to some aspects of cognitive behavior or mating behavior in mammals. The present disclosure shows that *Ginkgo* crude extracts and certain chemicals in *Ginkgo* extract may be used as pest deterrents in the apple industry (apple breeding, processing, retail and consumption). In addition, some *Ginkgo* flavonoids may also have insect deterrent properties.

In one embodiment, metabolites of *Ginkgo biloba*, such as Ginkgolic acid 15:0, bilobalide and ginkgolide B, may be used for preventing apple infestation by codling moth. These chemicals may act alone or in combination as deterrents to prevent the codling moth larvae from entering the apples treated with solutions of these chemicals.

These chemicals may be formulated as a spray and may be directly sprayed onto apples.

In another embodiment, the genes encoding proteins involved in the synthesis of one or more of these chemicals may be used for bioengineering of apple trees so that the engineered apples become unpalatable to codling moth larvae.

In another embodiment, a composition containing one or more molecules derived from a tissue of *ginkgo* may be prepared or synthesized. The tissue may be any tissue, such as, by way of example, fruits, seeds, leaves, flowers, or stems. The chemicals may be isolated from a tissue of *ginkgo* or they may be synthesized in an artificial process. In one aspect, the synthetic molecules may be identical to molecules that naturally exist in the *ginkgo* plant. In another aspect, the synthetic molecules may be modified based on the molecules that naturally exist in the *ginkgo* plant. In one aspect, the composition may contain one or more molecules selected from the group consisting of alkylphenol and ginkgolide and bilobalide, wherein the molecule or molecules are present in the composition in an amount effective in deterring moth infestation.

In one aspect, the composition may further contain wax. In another aspect, apple may be bioengineered such that the *Ginkgo* secondary metabolites may be expressed in waxes that cover the apple peel.

In another embodiment, the molecule is present in the composition at a concentration of from about 0.01 mg/ml to about 10 mg/ml, or alternatively, at a concentration of from about 0.1 mg/ml to about 1 mg/ml, or to about 10 mg/ml.

In another embodiment, a method for controlling growth or infestation of a pathogenic organism is disclosed, wherein the pathogenic organism is exposed to a composition obtained from a tissue of *Ginkgo* plant, and wherein the composition contains at least one compound selected from the group consisting of alkylphenol, ginkgolide and bilobalide. In another aspect, kaempferol and/or quercetin may be removed from the composition.

In another embodiment, the timing of the treatment may depend on several factors, such as geographical location, climate, altitude, etc. Most codling moths, depending on the geographical location, have two generations per year and may attack the apple twice a year. The first generation usually corresponds with fruit setting and the second generation typically coincides with fruit shortly before harvest. The exact timing of infestation may be predicted by monitoring codling moth population dynamics with pheromone traps and day-degree calculation. In one embodiment, the composition may be applied to individual trees or to a field two times per year. Each application may contain one or two sprays.

DETAILED DESCRIPTION

Figure 1:
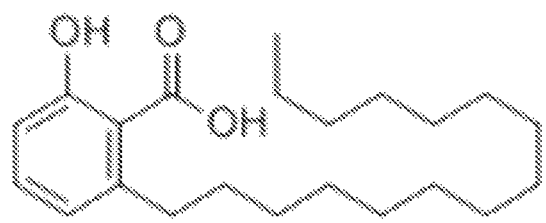
FIG. 1 shows the chemical structures of three *Ginkgo* metabolites: Ginkgolic acid 15:0, Ginkgolide B and Bilobalide.
Figure 1:
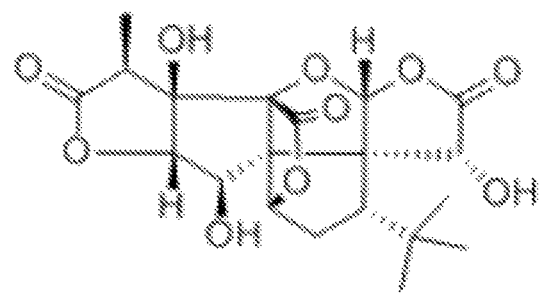
Figure 1:
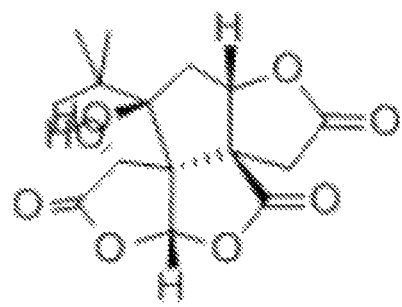

Many plants, including *Ginkgo*, are widely used as herbal medicine for humans. Little is known about the effect of *Ginkgo* derived chemicals in insects or other non-human organisms. Disclosed here are molecules that affect the behavior of certain apple-feeding moth. Many of the molecules disclosed herein may be derived from plants, or more specifically, from *Ginkgo*. The fact that such molecules have already been used in medicine should facilitate the process of their registration for pest management due to minimum side effects on humans.

Several *Ginkgo* herbal products marketed as EGb 761 extracts have been tested for their capability to deter codling moth. EGb 761 typically contains 24% of flavonol glycosides, 6% of terpene trilactones and no more than 5 ppm of alkylphenols (Stumpf, 1997). One of these extracts, which contains exceptionally high amounts of alkylphenols, has been found to have deterrent effects in the tests. In particular, the insect deterrent activities of terpene trilactones, flavonoids and alkylphenols fractions of this extract have been studied. In addition, insect deterrent activities of synthetic *Ginkgo* terpene trilactones, flavonoids and alkylphenols known to be present in EGb 761 have also been investigated.

In one embodiment, crude extract from standardized *Ginkgo* prevents apple infestation by codling moth neonates in a dosage-dependent manner, exhibiting deterrent properties at concentration as low as 1.5 mg/ml and 3 mg/ml. At a concentration of 10 mg/ml, over 90% of neonates avoid the fruit treated with the extract, while at higher concentrations, the crude extract completely prevents fruit infestation by the codling moth. By contrast, crude extract from *A. absinthium* exhibits deterrent properties against codling moth neonates only at 30 and 10 mg/ml but were inactive at concentrations of 3 mg/ml or 1 mg/ml (Durden et al., 2009).

Individual chemical components in crude *Ginkgo* extract have been further studied and the results are disclosed here. In one embodiment, alkylphenol extract is a strong deterrent at 2 mg/ml and 5 mg/ml, indicating that some *Ginkgo* alkylphenols may be used as a deterrent against codling moth neonates. In another embodiment, ginkgolic acid 15:0 shows strong insect deterrent properties at concentrations ranging from 1 to 5 mg/ml. Note that saturated ginkgolic acids work better as a deterrent against codling moth neonates than unsaturated ginkgolic acids.

Crude terpene trilactons may also be used as a deterrent to codling moth at relatively low concentration, for example, at 1 mg/ml, and this action may be explained by feeding deterrent action of bilobalide and that of ginkgolide B.

*Ginkgo* flavonol glycosides show none or very weak deterrent effects against codling moth neonates, and show some deterrent effects only at relatively high concentration, for example, at 10 mg/ml. Some components, for example, kaempferol and quercetin, show some stimulatory effects on codling moth neonates, while isorhamnetin only shows negligible deterrent effects. Feeding-stimulatory effects of quercetin may be partially explained by the fact that this flavonol glycoside is present in apple peel (Boyer and Liu, 2004). It is known that codling moth neonates use gustatory stimuli in the process of fruit selection (Pszczolkowski and Brown, 2005) and the stimuli from quercetin may help in location or assessment of quality of the fruit prior to its infestation by this insect. It may be desirable to remove these chemicals that show stimulatory effects from crude *Ginkgo* extracts before using *Ginkgo* extracts as a deterrent against codling moth neonates.

In another embodiment, two *Ginkgo* metabolites show promising potential in preventing fruit infestation by codling moth neonates. These two metabolites are ginkgolic acid 15:0 and bilobalide. Interestingly, both compounds exert insect deterrent properties at relatively low concentrations of 0.01% and 0.1%, thus there is a potential of their use in codling moth control even as direct sprays, particularly by environmentally conscious amateur growers. By contrast, most other "green" insect controlling products are applied at 0.5% and higher concentrations, reaching sometimes 70%. This strategy is particularly appealing in the case of bilobalide, since this compound is nontoxic to mammals ($LD_{50}$, >1,000 mg/kg), is not mutagenic and is not phytotoxic at concentration of 0.2% (Ahn et al., 1997).

Moreover, numerous recent works on cloning and functional analysis of the *Ginkgo* terpene trilactones biosynthetic genes (Wang et al., 2004; Liao et al., 2004; Kim et al., 2006; Shen et al, 2006; Gong et al, 2006) have been paving the way to improving production of these compounds by *Ginkgo* genetic engineering. Some progress has been also made toward expressing ginkgolic acid in yeasts (Wan et al., 2009). On the other hand, apple genome has been recently sequenced (Velasco et al., 2010) and reconstruction of the complete biosynthetic pathways for ginkgolic acids or bilobalide in transgenic apple may be a desirable way to generate apples that are inherently resistant to infestation by codling moth.

In one embodiment, proteins responsible for the making of ginkgolic acids or bilobalide may be expressed in apples. In one aspect, the transgenic expression may be controlled such that the amounts of ginkgolic acids or bilobalide are high enough for making the fruit unpalatable to codling moth larvae. In another aspect, the concentrations of the ginkgolic acids or bilobalide are controlled such that they are low enough and are still acceptable for consumers. The fact that *Ginkgo* constituents have therapeutic values should contribute to minimizing undesirable side effects of such genetic modification on consumer health. Bilobalide can be safely consumed at relatively high rates (Sierpina et al., 2003), and has been shown to have strong neuroprotective effects (Ahlemeyer and Krieglstein, 2003) and strong antioxidant activity when used alone or in combination with apple flavonoids (Mahadevan and Park, 2008).

Ginkgolic acids have caused some safety concerns. These compounds are suspected to have cytotoxic, allergenic and mutagenic effects (Chao and Chu, 2004). On the other hand, some homeopathic formulations of *Ginkgo* extracts contain as much as 2.2% of ginkgolic acids (40,000 times higher concentration than that considered safe!) (Siegers 1999) and no reports have been filed on adverse effects of such tinctures (Woerdenbag and van Beek, 1997; Woerdenbag and de Smet, 2000). Moreover, as non-polar compounds, ginkgolic acids may be expressed in apple waxes that can be removed before the fruit reaches the consumer as it is done presently.

EXAMPLES

The following examples illustrate the present disclosure. These examples are provided for purposes of illustration only and are not intended to be limiting. The chemicals and other ingredients are presented as typical components or reactants, and various modifications may be derived in view of the foregoing disclosure within the scope of the invention.

Example 1

Bioassays to Determine Effects of Various Plant Extracts on Infestation by Codling Moth Codling moth pupae were obtained from USDA-ARS Yakima Agricultural Research Laboratory in Wapato, Wash., USA. These pupae were stored at 25° C., 70-80% relative humidity and 16:8 (L:D). Moths were allowed to oviposit on polypropylene Ziploc bags (S. C. Johnson, Racine, Wis., USA). Neonates were collected 0.5-1.0 h post-hatch and subjected to bioassays immediately.

Dehydration alcohol (a V/V mixture of 80% ethanol, 10% isopropanol and 10% of methanol) was purchased from EMD, Gibbstown, N.J., USA. Ginkgolic acids 13:0, 15:0, and 17:1, and ginkolid C were purchased from Nacalai USA (San Diego, Calif., USA), Ginkgolic acid 15:1 was purchased from Alexis Biochemicals, (San Diego, Calif., USA). Remaining reagents were purchased from Sigma-Aldrich (St Louis, Mo., USA).

Standardized *Ginkgo* extracts were purchased from local grocery stores as five batches of tablets or capsules marketed by Nature's Bounty, Bohemia, N.Y., USA and AJG Brands, Boca Raton, Fla., USA. One hundred fifty milligrams (mg) of the powder obtained by crushing the tablet or opening the capsule were placed in a 2 ml eppendorf tube with 1 ml of dehydration alcohol, vortexed briefly, allowed to rest for 10 min at room temperature and centrifuged at 2000 G for 10 min. The liquid fraction was pipetted off, transferred to a pre-weighed eppendorf tube and evaporated in a SpeedVac rotary evaporator. After desiccation, eppendorf tubes were re-weighed to determine the final mass of the residue which was subsequently re-suspended with dehydration alcohol to the desired concentration. For further studies, the extracts were coded as A, B, C, D and E, depending on the lot number, the manufacturer and the retailer.

Bioassays were performed as described in details by Durden et al. (2008). Briefly, apple plugs were formed by forcing a plastic soda straw through a 20 mm thick section of apple containing both epidermis and flesh of the apple. The straw with a plug in it was cut to a length of approximately 15 mm, the plug positioned with the epidermis of the apple protruding 2 mm from the straw and entire assembly was dipped in liquid paraffin wax. Excess wax was removed from the epidermis of the plug using a warm spatula.

Five microliters of either control (dehydration alcohol only) or experimental solution was applied to the epidermis of each apple plug and allowed to dry. Using a small amount of modeling clay, four plugs (two controls, two experimental) were arranged with one control and one experimental plug facing each other at either side of a 60×15 mm polyurethane petri dish. A short piece of glass rod (1.3 mm diameter) was placed between the two pairs of plugs to form a bridge allowing tested codling moth neonate to choose between either control or experimental plug regardless of which direction the larva traveled along the glass rod. Single codling moth neonate was placed with a fine camel brush, on the glass rod, equidistant from the apple plug pairs, the petri dish was covered, placed upon a light table and covered with a semi-translucent dome to avoid a non-directional light source which could bias the results as codling moth neonates are known to exhibit mild phototropism (Jackson, 1982).

Assays were evaluated after 20 hours to determine which plug was fed upon. Feeding deterrence index was calculated according to Jones (1952) by dividing the number of the neonates feeding on apple plugs treated with *Artemisia* extracts by the number of the neonates feeding on the plugs treated with dehydration alcohol only, subtracting this figure from 1, and multiplying the result by 100. Further details about this method may be found in Durden et al. (2008) and Durden et al., (2011).

Five different crude *Ginkgo* extracts were bioassayed for insect deterrent activity at 10 mg/ml. Twenty to 32 larvae were used for each extract testing. Four extracts (coded B, C, D and E) did not show statistically significant insect deterrent properties, but extract A effectively prevented fruit infestation: out of 25 codling moth neonates tested, only one infested extract-treated plug (P<0.01, Fisher Exact test). Qualitative High Performance Thin Layer Chromatography (HPTLC) using procedure recommended by CAMAG for visualization of ginkgolic acids, (Camag Application Notes, 2003, see also following paragraph for the details) showed significant presence of alkyphenols and other polar constituents in extract A.

Using HPTLC and serial dilution method (Kirchner et al., 1954), it was found that extract A contained at least 1% of total alkylphenols, which is in accordance with van Beek (2002) who states that some *Ginkgo* homeopathic products available on specialty markets may contain up to 2.2% of total alkylphenols. Extract A was produced in a form of 600 mg tablets by Nature's Bounty, Bohemia, N.Y., USA (lot number 65229 02) and withdrawn from retail in 2007. Crude alcohol extract from these tablets is referred to as "crude standardized *Ginkgo* extract" throughout the remaining part of this paper and was either subjected to bioassays for insect deterrence in a dose-dependent manner or to crude extraction of alkylphenols, flavonol glycosides or terpene trilactones.

TABLE 1

Effects of crude extracts from *Ginkgo biloba* on apple feeding by codling moth neonates.

| Type of crude extract and concentration | Number of neonates feeding | | |
|---|---|---|---|
| (mg/ml) | Treated fruit | Control fruit | Deterrence index |
| Crude standardized | | | |
| 45 | 0*** | 20 | 100 |
| 15 | 0*** | 20 | 100 |
| 10 | 1** | 12 | 91.7 |
| 3 | 3* | 11 | 72.7 |
| 1.5 | 9* | 28 | 67.9 |
| 0.3 | 12 | 15 | 20.0 |
| 0.03 | 13 | 15 | 13.0 |
| Alkylphenols | | | |
| 5 | 1*** | 19 | 94.7 |
| 2 | 4*** | 29 | 86.2 |
| 1 | 11 | 23 | 52.2 |
| 0.2 | 10 | 18 | 44.4 |
| 0.1 | 11 | 14 | 21.4 |
| Flavonol glycosides | | | |
| 10 | 10** | 34 | 70.6 |
| 3 | 8 | 12 | 33.3 |
| 1 | 18 | 17 | Not deterrent |
| 0.1 | 6 | 7 | 14.3 |
| 0.3 | 10 | 10 | 0 |
| Terpene trilactones | | | |
| 10 | 7** | 35 | 80.0 |
| 3 | 12* | 32 | 62.5 |
| 1 | 11** | 34 | 67.6 |
| 0.1 | 14 | 29 | 51.7 |
| 0.01 | 25 | 33 | 24.2 |

*P < 0.05,
**P < 0.01,
***P < 0.001 in Fisher's Exact Test

*Ginkgo* extracts were tested for deterrent effects at concentrations ranging from 0.01 to 60 mg/ml. The number of tests per concentration (each test performed with a different neonate) varied between 13 and 93. The null hypothesis that 50% of neonates would choose control plugs and 50% would choose experimental plugs was tested using Fisher's Exact Test ($\alpha$=0.05).

Crude standardized extract from *Ginkgo* prevented fruit feeding at concentrations equal or higher than 1.5 mg/ml. (Table 1, N=13-37, P<0.05, Fisher exact test). Concentrations 0.3 and 0.03 had slight deterrent effect numerically, but these effects were not statistically significant.

Example 2

Bioassays to Determine Effects of Alkylphenols from *Ginkgo* Extracts on Infestation by Codling Moth Alkylphenols were extracted from crude standardized *Ginkgo* extract by partitioning with hexane (van Beek, 2002) and subsequent HPTLC of the hexane fraction. Briefly, 400 µl of crude extract was placed in an eppendorf tube into which 100 µl of double-distilled water was added. Next, 1 ml of hexane was added to the tube, the mixture was vortexed for one minute, allowed to rest at room temperature for 10 minutes, centrifuged at 2000 G for 10 minutes and hexane fraction was collected to a separate tube, evaporated in Speedvac rotor evaporator and dissolved to desired concentration in dehydration alcohol.

Because partitioning to hexane also extracts fat-soluble constituents of *Ginkgo* other than alkylphenols, the procedure described above was followed by HPTLC using procedure recommended by CAMAG (Camag Application Notes, 2003). Briefly, 5 µl of hexane fraction and 0.1 mg/ml of ginkgolic acid 15:1 as standard were applied onto Merck 10×10 cm silica gel 60 $F_{254}$ glass plates with Camag Nanomat 4 HPTLC plate spotter. The plates were developed for 6 minutes in Camag Twin Trough 10×10 cm Horizontal Development Chamber (CAMAG Scientific Inc., Wilmington, N.C., USA) with 5 ml of mobile phase (Toluene, ethyl acetate, and acetic acid in a V/V ratio of 8:2:0.2) and allowed to air dry. The plates were inspected at UV 366 nm, the bands corresponding to the standard cut of the plate and collected into an eppendorf tube. Alkylphenols were then eluted from these cutouts with methanol (van Beek, 2002). Next, the methanol fraction was collected using a separate tube, evaporated in SpeedVac rotor evaporator and dissolved to desired concentration in dehydration alcohol.

Crude alkylphenol extract showed strong deterrent effects at 2 and 5 mg/ml with deterrence index 86 and 95, respectively (Table 1, N=20-33, P<0.001). Lower concentrations were ineffective.

Example 3

Bioassays to Determine Effects of Flavonol Glycosides from *Ginkgo* Extracts on Infestation by Codling Moth Flavonol glycosides from crude *Ginkgo* extracts were obtained using the procedure of Zhang et al., (2007). Briefly, 40 mg of evaporated crude standardized *Ginkgo* extract was dissolved in 2 ml of 50% aqueous methanol. The mixture was concentrated and dried in Speedvac rotor evaporator. The residue was then dissolved in 1 ml water and extracted with ethyl acetate three times (3×600 µl). The ethyl acetate layers were combined and evaporated to dryness in Speedvac rotor evaporator and dissolved to desired concentration in dehydration alcohol.

As shown in Table 1, Crude flavonol glycosides had moderate deterrent properties only at 10 mg/ml with deterrence index about 70 (Table 1, N=44, P<0.01).

Example 4

Bioassays to Determine Effects of Terpene Trilactones from *Ginkgo* Extracts on Infestation by Codling Moth The procedure of Lichtblau et al., (2002) was used to obtain terpene trilactones from crude *Ginkgo* extracts.

Briefly, 25 ml of crude standardized *Ginkgo* extract were boiled for 1 hour in 0.5 L of 5% aqueous $H_2O_2$. After passing through a Buchner funnel, the remaining solution was extracted three times with ethyl acetate (250/125/75 ml). The organic layer was washed with a saturated solution of $Na_2SO_3$ followed by water and 80% aqueous NaCl (saturated aqueous solution diluted to 80%). After drying over $Na_2SO_4$, solvent was removed to yield an amorphous yellow powder which was subsequently dissolved to desired concentration in dehydration alcohol.

As shown in Table 1, deterrent effects of terpene trilactones were found at 1, 3 and 10 mg/ml (Table 1, N=42-45, P<0.01, Fisher exact test) with deterrence index ranging from 63 to 80.

Example 5

Bioassays to Determine Effects of Synthetic *Ginkgo* Alkylphenols on Infestation by Codling Moth The effects of synthetic *Ginkgo* alkylphenols were studied. Ginkgolic acid 15:0 (FIG. 1) had feeding deterrent effects against codling moth neonates at 1, 2 and 5 mg/ml (Table 2, N=13-24, P<0.05, Fisher exact test). Lower concentrations (about 0.5 mg/ml or lower) of ginkgolic acid 15:0 had no significant effect (Table 2). Deterrence indexes of 1-5 mg/ml ginkgolic acid 15:0 ranged from 74 to 92. Ginkgolic acid 15:1, ginkgolic acid 13:0, and ginkgolic acid 17:1 did not exhibit significant feeding deterrent properties against codling moth neonates (Table 2, N=26-40, P>0.05, Fisher exact test).

TABLE 2

Effects of synthetic *Ginkgo biloba* alkylphenols on apple feeding by codling moth neonates.

| Type of alkylphenol and concentration | Number of neonates feeding | | |
|---|---|---|---|
| (mg/ml) | Treated fruit | Control fruit | Deterrence index |
| Ginkgolic acid 15:0 | | | |
| 5 | 4** | 22 | 81.8 |
| 2 | 5* | 19 | 73.7 |
| 1 | 1* | 12 | 91.7 |
| 0.5 | 11 | 15 | 26.7 |
| 0.2 | 12 | 16 | 25.0 |
| Ginkgolic acid 15:1 | | | |
| 10 | 7 | 19 | 63.2 |
| 5 | 15 | 30 | 50.0 |
| 1 | 14 | 24 | 41.7 |
| 0.5 | 13 | 16 | 18.8 |
| Ginkgolic acid 13:0 | | | |
| 10 | 11 | 19 | 42.1 |
| 5 | 14 | 14 | 0 |
| 1 | 17 | 23 | 26.1 |
| 0.5 | 13 | 17 | 23.5 |
| Ginkgolic acid 17:1 | | | |
| 10 | 8 | 20 | 60.0 |
| 5 | 10 | 22 | 54.5 |
| 1 | 18 | 19 | 5.3 |
| 0.5 | 10 | 16 | 37.5 |

*P < 0.05,
**P < 0.01,
***P < 0.001 in Fisher's Exact Test

Example 6

Bioassays to Determine Effects of Synthetic *Ginkgo* Flavonol Glycosides on Infestation by Codling Moth The effects of synthetic *Ginkgo* flavonol glycosides were also determined. Numerically, isorhamnetin showed slight tendency to discourage some percentage of the larvae from infesting the fruit, but when analyzed with Fisher exact test, none of synthetic *Ginkgo* flavonol glycosides exhibited statistically significant deterrent properties (Table 3, N=20-71, P>0.05). On the contrary, kaempferol and quercetin had statistically significant feeding stimulatory effects and facilitated fruit infestation at 10 mg/ml and higher concentrations. Removing kaempferol and quercetin from crude extracts of *ginkgo* may enhance their inhibitory effects against codling moth.

TABLE 3

Effects of synthetic *Ginkgo biloba* flavonol glycosides on apple feeding by codling moth neonates.

| Type of flavonol glycoside and concentration | Number of neonates feeding | | |
|---|---|---|---|
| (mg/ml) | Treated fruit | Control fruit | Deterrence index |
| Kaempferol | | | |
| 60 | 17 | 3 | No deterrence* |
| 30 | 35 | 9 | No deterrence** |
| 10 | 10 | 10 | No deterrence |
| 1 | 24 | 32 | 25 |
| 0.1 | 12 | 8 | No deterrence |
| Quercetin | | | |
| 30 | 21 | 4 | No deterrence** |
| 10 | 20 | 16 | No deterrence |
| 1 | 24 | 24 | No deterrence |
| 0.1 | 14 | 10 | No deterrence |
| Isorhamnetin | | | |
| circa 3† | 19 | 28 | 32.1 |
| 1 | 43 | 28 | No deterrence |
| 0.1 | 26 | 29 | 10.3 |
| 0.01 | 18 | 23 | 21.7 |

†saturated solution statistically significant feeding stimulation was found at *P < 0.05 or **P < 0.01 in Fisher's Exact Test Example 7

Bioassays to Determine Effects of Synthetic *Ginkgo* Terpene Trilactones on Infestation by Codling Moth The effects of synthetic *Ginkgo* terpene trilactones on codling moth were determined. Ginkgolide B (FIG. 1) showed significant feeding deterrent properties against codling moth neonates at 10 mg/ml, but not at lower concentrations (Table 4, N=31, P<0.001, Fisher exact test). Bilobalide (FIG. 1) had deterrent properties at wider range of concentrations ranging from 0.1 to 10 mg/ml (Table 4, N=42-93, P<0.01, Fisher exact test), with significant deterrent properties at concentration as low as 0.1 mg/ml. Ginkgolide A and ginkgolide C did not exhibit significant feeding deterrent properties against codling moth neonates (Table 4, N=22-75, P>0.05, Fisher exact test).

TABLE 4

Effects of synthetic Ginkgo terpene trilactones on apple feeding by codling moth neonates.

| Type of terpene trilactones and concentration | Number of neonates feeding | | |
|---|---|---|---|
| (mg/ml) | Treated fruit | Control fruit | Deterrence index |
| Ginkgolide A | | | |
| 10 | 16 | 26 | 38.5 |
| 1 | 28 | 47 | 40.4 |
| 0.1 | 12 | 13 | 7.69 |
| Ginkgolide B | | | |
| 10 | 6*** | 25 | 76.0 |
| 1 | 17 | 23 | 26.1 |
| 0.1 | 14 | 16 | 12.5 |
| Ginkgolide C | | | |
| 10 | 18 | 20 | 10 |
| 1 | 24 | 30 | 20 |
| 0.1 | 15 | 17 | 11.8 |
| Bilobalide | | | |
| 10 | 8** | 32 | 75 |
| 1 | 31* | 62 | 50 |
| 0.1 | 20* | 46 | 56.5 |
| 0.01 | 13 | 17 | 23.5 |
| 0.001 | 15 | 15 | 0 |

*$P < 0.05$,
**$P < 0.01$,
***$P < 0.001$ in Fisher's Exact Test

Example 8

Timing and Dosage of Treatment

The timing for applying the ginkgo derived composition to apple trees may depend on several factors, such as geographical location, climate, altitude, etc. Most codling moths have two generations each year, and may attack the apple two times a year. The first generation usually corresponds with fruit setting and the second generation typically occurs shortly before harvest of the fruits. The exact timing of infestation may be determined by monitoring codling moth population dynamics with pheromone traps and day-degree calculation. In one embodiment, the composition may be applied to individual trees or to a field two times per year. Each application may contain one or two sprays.

Figure 2:
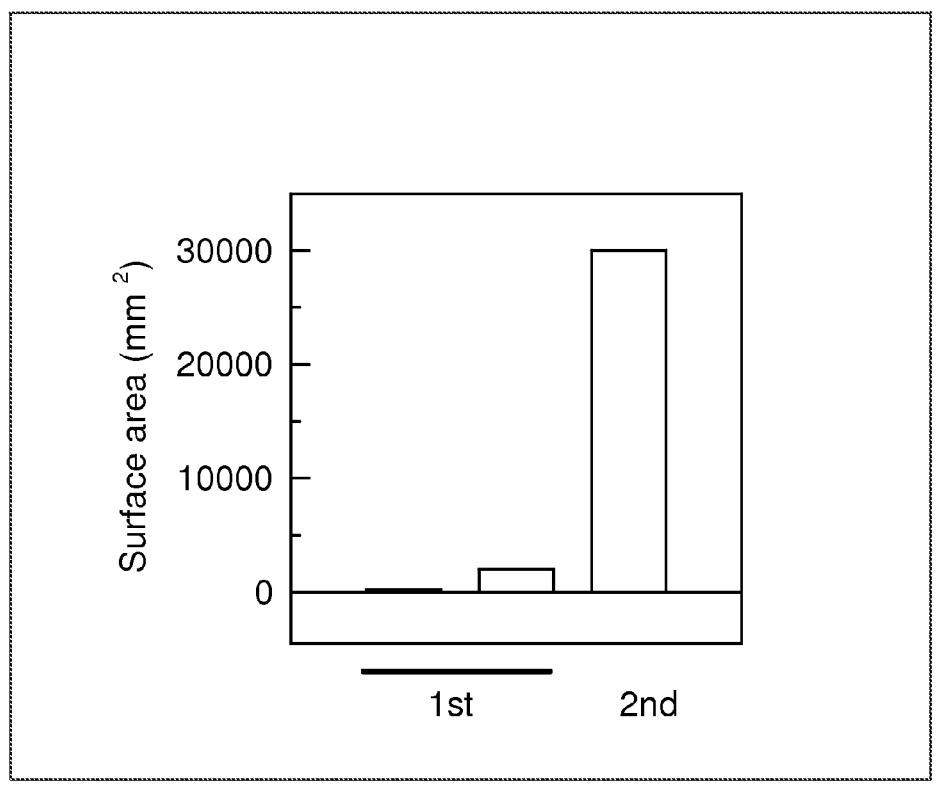
FIG. 2 shows the change of surface areas of an apple fruit during the first and second generation of codling moth infestation.

The timing of application of the disclosed composition to fruit trees (e.g., apple) may have some effects on field doses of Ginkgo-based repellents. As an apple fruit grows, the surface area of the apple also increases. A simple estimation shows that the apples during second generation outbreak may have about 100 times larger surface area than the surface area of the fruits during first generation outbreak (see FIG. 2). These data suggest that the field dosage or the per-apple dosage of the repellent for controlling second generation may be higher than the dosage against first generation infestation.

Changes may be made in the above compositions and methods without departing from the scope hereof. It should thus be noted that the matter contained in the above description should be interpreted as illustrative and not in a limiting sense.

REFERENCES

All references cited throughout the text or listed below are hereby incorporated into this disclosure as if fully reproduced herein.

Ahlemeyer B, Krieglstein J. Neuroprotective effects of Ginkgo biloba extract. Cell Mol Life Sci 2003; 60:1779-92.

Ahn Y-J, Kwon M, Park, H-M, Han C-K. Potent insecticidal activity of Ginkgo biloba derived trilactone terpenes against Nilaparvata lugens. In: Phytochemicals for Pest Control, ACS Symposium Series, American Chemical Society, 1997, 90-105.

Chao J C, Chu C C. Effects of Ginkgo biloba extract on cell proliferation and cytotoxicity in human hepatocellular carcinoma cells. World J Gastroentero 2004; 10:37-41.

Fu-shun Y, Evans K A, Stevens L H, Beek T A, Schoonhoven L M. Deterrents extracted from the leaves of Ginkgo biloba: effects on feeding and contact chemoreceptors. Entomol Exp Appl 1990; 54:57-64.

Gong Y F, Liao Z H, Guo B H, Sun X F, Tang K X. Molecular cloning and expression profile analysis of Ginkgo biloba DXS gene encoding 1-deoxy-D-xylulose 5-phosphate synthase, the first committed enzyme of the 2-C-methyl-D-erythritol 4-phosphate pathway. Planta Med 2006; 72:329-35.

Kim S M, Kuzuyama T, Chang Y J, Song K S, Kim S U. Identification of class 2 1-deoxy-D-xylulose 5-phosphate synthase and 1-deoxy-D-xylulose 5-phosphate reductoisomerase genes from Ginkgo biloba and their transcription in embryo culture with respect to ginkgolide biosynthesis. Planta Med. 2006; 72:234-40.

Liao Z, Chen M, Gong Y, Guo L, Tan Q, Feng X, Sun X, Tan F, Tang K. A new geranylgeranyl diphosphate synthase gene from Ginkgo biloba, which intermediates the biosynthesis of the key precursor for ginkgolides. DNA Seq 2004; 15:153-8.

Mahadevan S, Park Y. Multifaceted therapeutic benefits of Ginkgo biloba L.: chemistry, efficacy, safety, and uses. J Food Sci 2008; 73:R14-9.

Major R T. The ginkgo, the most ancient living tree. The resistance of Ginkgo biloba L. to pests accounts in part for the longevity of this species. Science 1967; 157:1270-3.

Matsumoto T, Sei T. Antifeedant activities of Ginkgo biloba L. components against the larva of Pieris rapae crucivora. Agric Biol Chem 1987; 51:249-50.

Onyilagha J C, Lazorko J, Gruber M J, Soroka J J, Erlandson M A. Effect of flavonoids on feeding preference and development of the crucifer pest Mamestra configurata Walker. J Chem Ecol 2004; 30:109-24.

Poullot D, Beslay D, Bouvier J-C, Sauphanor B. Is attract and kill technology potent against resistant Lepidoptera? Pest Manag Sci 2001; 57: 729-36.

Schultz D J, Olsen C, Cobbs G A, Stolowich N J, Parrott M M. Bioactivity of anacardic acid against Colorado potato beetle (Leptinotarsa decemlineata) larvae. J Agric Food Chem 2006; 54:7522-9.

Shen G, Pang Y, Wu W, Liao Z, Zhao L, Sun X, Tang K. Cloning and characterization of a root-specific expressing gene encoding 3-hydroxy-3-methylglutaryl coenzyme A reductase from Ginkgo biloba. Mol Biol Rep 2006; 33:117-27.

Shimada T, Hayes C L, Yamazaki H, Amin S, Hecht S S, Guengerich F P, Sutter T R. Activation of chemically diverse procarcinogens by human cytochrome P-450 1B1. Cancer Res 1996; 56:2979-84.

Siegers C P. Cytotoxicity of alkylphenols from Ginkgo biloba. Phytomedicine 1999; 6:281-3.

Sierpina V S, Wollschlaeger B, Blumenthal M. Ginkgo biloba. Am Fam Physician 2003; 68:923-6.

Simmonds M S. Importance of flavonoids in insect-plant interactions: feeding and oviposition. Phytochemistry 2001; 56:245-52.

Simmonds M S. Flavonoid-insect interactions: recent advances in our knowledge. Phytochemistry 2003; 64:21-30.

van Beek T A. (2002). Chemical analysis of *Ginkgo biloba* leaves and extracts. J Chromatogr A. 2002; 967:21-55

Velasco R, Zharkikh A, Affourtit J, Dhingra A, Cestaro A, Kalyanaraman A, Fontana P, Bhatnagar S K, Troggio M, Pruss D, Salvi S, Pindo M, Baldi P, Castelletti S, Cavaiuolo M, Coppola G, Costa F, Cova V, Dal Ri A, Goremykin V, Komjanc M, Longhi S, Magnago P, Malacarne G, Malnoy M, Micheletti D, Moretto M, Perazzolli M, Si-Ammour A, Vezzulli S, Zini E, Eldredge G, Fitzgerald L M, Gutin N, Lanchbury J, Macalma T, Mitchell J T, Reid J, Wardell B, Kodira C, Chen Z, Desany B, Niazi F, Palmer M, Koepke T, Jiwan D, Schaeffer S, Krishnan V, Wu C, Chu V T, King S T, Vick J, Tao Q, Mraz A, Stormo A, Stormo K, Bogden R, Ederle D, Stella A, Vecchietti A, Kater M M, Masiero S, Lasserre P, Lespinasse Y, Allan A C, Bus V, Chagné D, Crowhurst R N, Gleave A P, Lavezzo E, Fawcett J A, Proost S, Rouzé P, Sterck L, Toppo S, Lazzari B, Hellens R P, Durel C E, Gutin A, Bumgarner R E, Gardiner S E, Skolnick M, Egholm M, Van de Peer Y, Salamini F, Viola R Velasco R, Zharkikh A, Affourtit J, Amit Dhingra A. et al., (2010) The genome of the domesticated apple (*Malus×domestica* Borkh.). Nat Genet 2010; 42: 833-9

Vogensen S B, Strømgaard K, Shindou H, Jaracz S, Suchiro M, Ishii S, Shimizu T, Nakanishi K. Preparation of 7-substituted ginkgolide derivatives: potent platelet activating factor (PAF) receptor antagonists. J Med Chem 2003; 46:601-8.

Wang P, Liao Z, Guo L, Li W, Chen M, Pi Y, Gong Y, Sun X, Tang K. Cloning and functional analysis of a cDNA encoding *Ginkgo biloba* farnesyl diphosphate synthase. Mol Cells 2004; 18:150-6

Wan X, Zhang Y, Wang P, Huang F, Chen H, Jiang M. Production of gamma-linolenic acid in *Pichia pastoris* by expression of a delta-6 desaturase gene from *Cunninghamella echinulata*. J Microbiol Biotechnol 2009; 19:1098-102.

Woerdenbag, H J, van Beek, T A *Ginkgo biloba*. In: de Smet PAGM, Keller K, Hänsel R, Chandler R F, editors. Adverse effects of herbal drugs, Vol. 3. Berlin: Springer; 1997. p. 51-66

Woerdenbag H J, de Smet, PAGM. Adverse Effects and Toxicity of *Ginkgo biloba*. In: *Ginkgo biloba*. van Beek T A, editor. Medicinal and Aromatic Plants—Industrial Profiles, Vol. 12, CRC Press; 2000 p. 443-52.

Wolfgang S. 1988 Apple Orchard Summary. Emmaus, P A: Rodale Research Center; 1989. P. 30-1.

What is claimed is:

1. A composition for inhibiting codling moth infestation, said composition comprising a coating material, alkylphenol and terpene trilactone, wherein said coating material is wax, and wherein said alkylphenol is a saturated ginkgolic acid, and wherein said ginkgolic acid is ginkgolic acid 15:0, said alkylphenol and terpene trilactone being present in an amount effective in preventing codling moth infestation, said composition being formulated into a form that is capable of being sprayed.

2. The composition of claim 1, wherein said alkylphenol and terpene trilactone are derived from a tissue of ginkgo.

3. The composition of claim 1, wherein the deterrence index of said composition is greater than 60% against apple codling moth.

4. The composition of claim 1, wherein said composition comprises an alkylphenol and said alkylphenol is present in said composition at a concentration of from about 2 mg/ml to about 5 mg/ml.

5. The composition of claim 1, wherein said composition further comprises ginkgolide B and said ginkgolide B is present in said composition at a concentration of at least about 10 mg/ml.

6. The composition of claim 1, wherein said composition further comprises a bilobalide and said bilobalide is present in said composition at a concentration of from about 0.1 mg/ml to about 10 mg/ml.

7. A method for preventing infestation of a plant by a pest, said method comprising (a) administering the composition of claim 1 to said plant.

8. The method of claim 7, wherein the pest is an insect.

9. The method of claim 7, wherein the pest is a codling moth.

10. The method of claim 7, wherein said alkylphenol being present in said composition at a concentration of from about 2 mg/ml to about 5 mg/ml.

11. The method of claim 7, wherein said composition further comprises ginkgolide B, said ginkgolide B being present in said composition at a concentration of at least about 10 mg/ml.

12. The method of claim 7, wherein said composition further comprises a bilobalide, said bilobalide being present in said composition at a concentration of from about 0.1 mg/ml to about 10 mg/ml.

13. A method for controlling growth of a pathogenic organism, said method comprising exposing said pathogenic organism to the composition of claim 1.

14. The method of claim 13, wherein the pathogenic organism is a codling moth.

* * * * *